(12) United States Patent
Lacour et al.

(10) Patent No.: US 7,106,439 B2
(45) Date of Patent: Sep. 12, 2006

(54) ELEMENTARY ANALYSIS DEVICE BY OPTICAL EMISSION SPECTROMETRY ON LASER PRODUCED PLASMA

(75) Inventors: Jean-Luc Lacour, Villabon/Yvette (FR); Jean-François Wagner, Drancy (FR); Vincent Detalle, Montreal (FR); Patrick Mauchien, Palaiseav (FR)

(73) Assignee: Commissariat a l'Energie Atomique, Paris (FR)

( * ) Notice: Subject to any disclaimer, the term of this patent is extended or adjusted under 35 U.S.C. 154(b) by 0 days.

(21) Appl. No.: 10/932,829

(22) Filed: Sep. 1, 2004

(65) Prior Publication Data

US 2005/0024638 A1 Feb. 3, 2005

Related U.S. Application Data

(63) Continuation of application No. 09/869,351, filed as application No. PCT/FR00/03056 on Nov. 2, 2000, now abandoned.

(30) Foreign Application Priority Data

Nov. 3, 1999 (FR) .................................. 99 13717

(51) Int. Cl.
*G01J 3/30* (2006.01)

(52) U.S. Cl. ...................... 356/318; 356/326; 359/739

(58) Field of Classification Search ............... 356/318, 356/311, 317, 326, 330, 300; 359/739; 250/372
See application file for complete search history.

(56) References Cited

U.S. PATENT DOCUMENTS

| 3,783,874 | A | 1/1974 | Koester et al. ................ 606/4 |
|---|---|---|---|
| 4,407,964 | A | 10/1983 | Elings et al. ................ 436/518 |
| 4,758,533 | A | 7/1988 | Magee et al. ................ 438/662 |
| 4,786,813 | A | 11/1988 | Svanberg et al. ........ 250/461.1 |
| 5,537,207 | A | 7/1996 | Carlhoff et al. .............. 356/317 |
| 5,583,634 | A | 12/1996 | Andre et al. ................. 356/318 |
| 5,657,304 | A | 8/1997 | Lehureau ............... 369/112.05 |
| 5,751,416 | A | 5/1998 | Singh et al. ................. 356/311 |
| 5,780,806 | A | 7/1998 | Ferguson et al. ....... 219/121.68 |
| 5,781,289 | A | 7/1998 | Sabsabi et al. ............. 356/318 |

FOREIGN PATENT DOCUMENTS

WO WO 01/33202 5/2001

OTHER PUBLICATIONS

F. L. Pedrotti, S. J. Pedrotti, 'Introduction to Optics', Prentice Hall, New Jersey, 1993, pp. 40-57.*

Cremers, et al., "Remote Elemental Analysis by Laser-Induced Breakdown Spectroscopy Using a Fiber-Optic Cable", Jun. 1995, 1369 Applied Spectroscopy, vol. 49, No. 6, pp. 857-860.

Marquardt et al., "Novel Probe for Laser-Induced Breakdown Spectroscopy and Raman Measurements Using an Imaging Optical Fiber", 1998, Applied Spectroscopy, vol. 52, No. 9, pp. 1148-1153.

(Continued)

Primary Examiner—Arnel C. Lavarias
(74) Attorney, Agent, or Firm—Thelen Reid & Priest LLP

(57) ABSTRACT

This device comprises a pulsed laser source (6), means (8, 10, 12) for focusing light from this source onto an object to be analysed (2) to produce plasma on the surface of the object, means (16, 18) of analyzing a plasma radiation spectrum, means (20) of determining the elementary composition of the object from this analysis, and possibly means (4) for displacing the object. The invention is particularly applicable to test radioactive materials.

15 Claims, 2 Drawing Sheets

OTHER PUBLICATIONS

"Study of Emission Spectroscopy on Laser Produced Plasma For Localised Multielemental Analysis in Solids with Surface Imaging", Nov. 1993-Apr. 1996, 14 pages.

Berndt et al., "Mikro-Emissionsspektralanalyse mit Festkorper-LASER", 1965, pp. 45-57.

* cited by examiner

ELEMENTARY ANALYSIS DEVICE BY OPTICAL EMISSION SPECTROMETRY ON LASER PRODUCED PLASMA

This application is a continuation and claims the benefit under 35 USC § 120 of application Ser. No. 09/869,351, filed Jun. 28, 2001 now abandoned, which is a 371 national stage application of PCT/FR00/03056, filed Nov. 2, 2000.

TECHNICAL FIELD

The invention relates to an elementary analysis device by optical emission spectrometry on laser produced plasma. This technique is carried out in a natural atmosphere.

It is particularly applicable to testing and in situ characterization of test pieces of parts to be analysed.

In particular, it is applied in the nuclear industry field for testing of radioactive materials.

In particular, the invention is applicable to mapping of MOX (Mixed Oxide) fuel pellets.

STATE OF PRIOR ART

The following document describing prior art, which the reader should refer to, describes an elementary analysis process for optical emission spectrometry on laser produced plasma in the presence of argon:

[1] EP 0654663A (invention by N. Andre, P. Mauchien and A. Semerok)—see also FR 2712697A and U.S. Pat. No. 5,583,634.

The technique divulged in this document cannot be used to test MOX fuel pellets with sufficient resolution and at sufficiently high speeds.

Remember that the MOX fuel used in nuclear reactors in the form of sintered MOX pellets contains a mix of plutonium oxide ($PuO_2$) and uranium oxide ($UO_2$).

The inspection on the fabrication of these pellets is an essential step in checking the specifications necessary for their use, particularly related to homogeneity of the $PuO_2$/$UO_2$ mix.

It is necessary to have an inspection technique for measuring and distributing the concentration of uranium and plutonium in pellets and satisfying the specification for their manufacturing process, the essential points of this process being as follows.

This technique must be capable of quantitatively describing objects with an average diameter of 10 µm. It can be demonstrated that a "probe" with a spatial resolution three times smaller than the diameter of a given object is necessary in order to precisely describe this object. This means that the diameter of the measurement point for an application for MOX pellets must be about 3 µm.

The chemical elements that must be measured quantitatively at this scale are uranium and plutonium.

The technique must enable the production of two-dimensional maps of pellets with different natures: firstly unbaked pellets (before entering into the furnace) that are brittle and porous, and secondly sintered pellets (after entering the furnace). The constraints for measurements on these two types of test pieces are very different.

Necessary preparation for the pellets to be analysed must be minimal, to be compatible with "on line" monitoring of an industrial manufacturing process. It must be possible to make the measurements remotely to prevent contamination of the measurement instrument.

It must be possible to inspect several units of pellets for a campaign lasting far one day in order to satisfy inspection needs. the minimum inspection area being equal to about 1 $mm^2$ per pellet.

Furthermore, it is desirable that the technique used should not generate any liquid radioactive effluents, that the nuclearised part of this technique should be minimized in order to limit work in the inspected area and that the measurement instrument should enable the analysis of radioactive test pieces without necessitating any particular preparation.

Three main techniques are known for inspecting the uniformity of MOX pellets.

The first two techniques are used to form the image of the surface of such a pellet. They make use of alpha autoradiography, that consists of measuring the emission of alpha particles by this pellet, and metallography attack that is a microscopic examination of a section of the pellet to which an acid treatment is applied (that leads to differentiated attack between $PuO_2$ and $UO_2$).

The third technique is used to make a quantitative surface micro-analysis and uses an electronic microprobe to analyse emission of X-radiation induced by electronic bombardment of the pellet.

Alpha autoradiography can only be used to obtain a qualitative image of elements emitting alpha particles. Thus, this technique detects all alpha emitters, for example such as plutonium and americium, without discrimination.

The resolution of this technique is of the order of 40 µm, which is not sufficient for the required performances (a few micrometers).

Thus, alpha autoradiography can only very partially satisfy the specification for inspection of MOX fuel pellets.

The reference technique for validating the fabrication process for sintered mixed plutonium and uranium oxide pellets is the analysis by electronic microprobe technique. The essential limitations of this technique are as follows:

Special preparation of test pieces to be analysed, which requires several hours of treatment, The long measurement period in quantitative analysis, several tens of hours being necessary for the analysis of a 1000 µm×250 µm map with a resolution of 3 µm, The impossibility of making concentration distribution measurements in unbaked pellets, the high porosity of this type of pellets making measurement by microprobe long and difficult.

Therefore, the electronic microprobe is not suitable for "in-line" inspection of the fabrication of MOX pellets.

Metallographic attack is relatively long to implement. Furthermore, it generates radioactive effluents in the case of an analysis of radioactive materials such as MOX fuel pellets.

Most surface inspection techniques use charged particle beams that make the analysis of insulators and poor conducting test pieces such as MOX pellets much more difficult. These techniques are used under a vacuum and are incapable of isolating the detection system that could become contaminated during measurements on radioactive test pieces and needs to be shielded to make it unaffected by radiation.

Optical methods, particularly optical emission spectrometry on laser produced plasma, are better adapted to the analysis of this type of material. In particular, the interaction of a laser beam with a material does not depend very much on the nature of this material. Furthermore, this interaction takes place at atmospheric pressure, and can be done directly in a glove box. The optical information resulting from this interaction can be collected by an optical fibre and analysed remotely by means of an instrument placed outside the radioactive confinement means. This can avoid contamination problems and facilitate maintenance.

The following document, to which the reader should refer, describes an elementary technique for analysis of solid test pieces by optical emission spectrometry on laser produced plasma:

[2] Measurement and Testing, contract MAT1-CT-93-0029, Study of emission spectroscopy on laser produced plasma for localized multielemental analysis in solids with imaging, November 1993–April 1996, Final report, project coordinator: C.E.A.—Seclay DCC/DPE (France).

According to the technique described in document [2], a laser beam is focused onto a diaphragm by a lens and then aimed at a Cassegrain type objective (reflecting objective) that has an optical resolution of the order of 2 μm. The laser beam is focused onto the diaphragm to create an image on the surface of the test piece that is a combination of the images of the laser and the diaphragm. This cannot be used to produce imagery smaller than 6 μm to 8 μm.

This type of assembly also requires extremely precise positioning of the lenses to achieve the best performances and frequent readjustments are necessary.

Furthermore, the Cassegrain objective has a central mirror that generates a central shadow area that causes a significant loss of the laser energy and thus limits the deposited energy or reduces the aperture used for the laser when working "off axis". Furthermore, the central mirror also generates diffraction. These points result in a loss of resolution.

The technique described in document [2] reduces the performances in terms of spatial resolution to the point that the system is unusable. It cannot achieve sufficient spatial resolution for use with mapping of MOX fuel pellets.

DISCLOSURE OF THE INVENTION

The purpose of this invention is to overcome the disadvantages described above and more generally to propose an elementary analysis device based on optical emission spectrometry on laser produced plasma capable of providing a high spatial resolution and usable for a high measurement rate while minimizing degradation to the surface condition of the analysed object.

Its purpose is an elementary analysis device by optical emission spectrometry on laser produced plasma, this device being characterized in that it comprises:

a pulsed laser source a diaphragm usable for selecting part of the laser beam emitted by the source, and possibly delimiting the shape of the impact of the laser beam on an object to be analysed, this laser beam not being focused in the plane of the diaphragm, first optical means capable of projecting the image of the diaphragm to infinity, second optical means designed to receive the image of the diaphragm projected to infinity by the first optical means and focusing it on the object to be analysed to produce plasma on the surface of this object, the assembly formed by the diaphragm and the first and second optical means also satisfying the following conditions:

the image of the diaphragm focused on the object is equal to the required dimension on this object (this dimension corresponding to the required spatial resolution, and for example being of the order of 1 μm to 10 μm)

the focal point of the laser beam, after crossing through the diaphragm and the first and second optical means, is outside the image plane of the diaphragm, means of analysing a light radiation spectrum emitted by the plasma, and means of determining the elementary composition of the object starting from this spectrum analysis.

The geometric lens entirely controls formation of the image of the diaphragm.

If the energy added by the laser beam is ignored, it can be seen that the diaphragm is a real object placed in front of a lens, preferably composed refractively of one or several lenses.

Therefore, this lens can be designed to project the image of the diaphragm to infinity.

On the other hand, the laser light beam that is not focused in the plane of the diaphragm will not be perfectly parallel when it exits from this lens.

Consequently, this beam will not be focused in the plane of the image of the diaphragm after passing through the second optical means.

Thus, it can be said that the optical set-up used means that the image plane of the diaphragm and the focal point of the laser do not coincide, so that the interaction size (analysis resolution) can be controlled.

The invention enables the laser source to cooperate with the diaphragm and the first and second optical means to create a single laser pulse on the object with an impact with a power per unit area equal to 1 $GW/cm^2$, this power per unit area preferably being equal to or greater than 10 $GW/cm^2$.

According to a preferred embodiment of the invention, the second optical means have a numerical aperture equal to or greater than 0.1.

The size of the impact of the laser beam on the object may be greater than or equal to 1 μm.

Preferably, it is equal to about 3 μm for application for MOX pellets.

However, in other applications, this size may vary from 1 μm to 10 μm.

Preferably, the displacement frequency of the object between two source laser pulses is greater than or equal to 15 Hz, in order to reduce the analysis time while creating synchronization of laser firing at the same rate.

A lower displacement frequency can also be used.

A plate controlling continuous or step-by-step displacement of the object can be used. If the plate is displaced continuously, the pitch of the analysis is proportional to the plate displacement speed, and is inversely proportional to the laser firing repetition frequency.

According to one preferred embodiment of the device according to the invention, the source can emit an ultraviolet light.

Preferably, the relative variation in the energy from one laser pulse to another does not exceed 5%.

According to one preferred embodiment of the invention:
the diaphragm comprises a circular aperture capable of selecting the central part of the laser beam output from the laser source,
the first optical means are refractive optical means, for example comprising a compound lens, and
the second optical means are refractive optical means comprising a microscope objective.

Preferably, the first and second optical means are anti-reflection treated at the wavelength of the light emitted by the laser source.

According to a third embodiment of the device according to the invention, this device also comprises means of blowing a gas jet capable of increasing optical emission of plasma (for example an argon jet) onto the object.

Preferably, the device also comprises:

means of observing the object, so that the object can be placed in the image plane of the diaphragm and a mirror reflecting at the wavelength of the laser source and transparent at other wavelengths, this mirror being placed on the light path between the first and second optical means and designed to reflect almost the entire laser beam to these second optical means and to transmit an image of the object to the observation means.

BRIEF DESCRIPTION OF THE DRAWINGS

This invention will be better understood after reading the following description of embodiments, given for information only and in no way restrictive, with reference to the attached drawings on which.

DETAILED DESCRIPTION OF PARTICULAR EMBODIMENTS

As we have seen, the invention is a device for optical emission spectrometry on laser produced plasma that can be used particularly for inspection of MOX fuel pellets.

In order to carry out a microanalysis by optical emission spectrometry on laser produced plasma, a pulsed laser beam is concentrated at the surface of a test piece to be characterized, with a high irradiance, once focused on the test piece in order to produce a plasma composed of elements present within the first micrometers from the surface of the test piece.

This plasma emits light radiation and the atomic and ionic lines of this radiation can be analysed in order to determine the corresponding concentrations of the different constituent elements on the surface of the test piece.

When the test piece is moved, the concentrations of these elements can be distributed in order to draw up the elementary maps.

This technique can be adapted to fast measurement of the distribution of the concentration of elements in MOX pellets with a resolution of 3 µm, so that according to the invention only one laser pulse per impact is necessary.

This characteristic of the invention is contrary to choices usually made in which it is preferred to use the average of several laser pulses for each impact.

The advantage of this procedure is that it reduces the analysis time and gives better control over the depth and diameter of pellet ablation craters.

Furthermore, in order to obtain representative measurements, the power per unit area. "deposited" on the pellet is greater than 10 GW/cm$^2$. Values of this order of magnitude can give ablation craters with a depth of only a few micrometers which do not significantly degrade the surface condition of the object.

These values can also be used to make measurements on an object for which the surface irregularities are of the same order of magnitude as the requested spatial resolution.

The means used to make measurements are chosen to be adapted to the laser powers used and to obtain impact sizes (diameter of ablation craters or lateral resolution) of about 3 micrometers.

Pellet displacement means are chosen to obtain a spectrum acquisition frequency equal to or greater than 15 Hz in order to improve the analysis speed.

These characteristics give optical emission spectrometry on laser produced plasma an undeniable advantage compared with the other techniques mentioned above, and make it capable of satisfying the needs.

Figure 1:
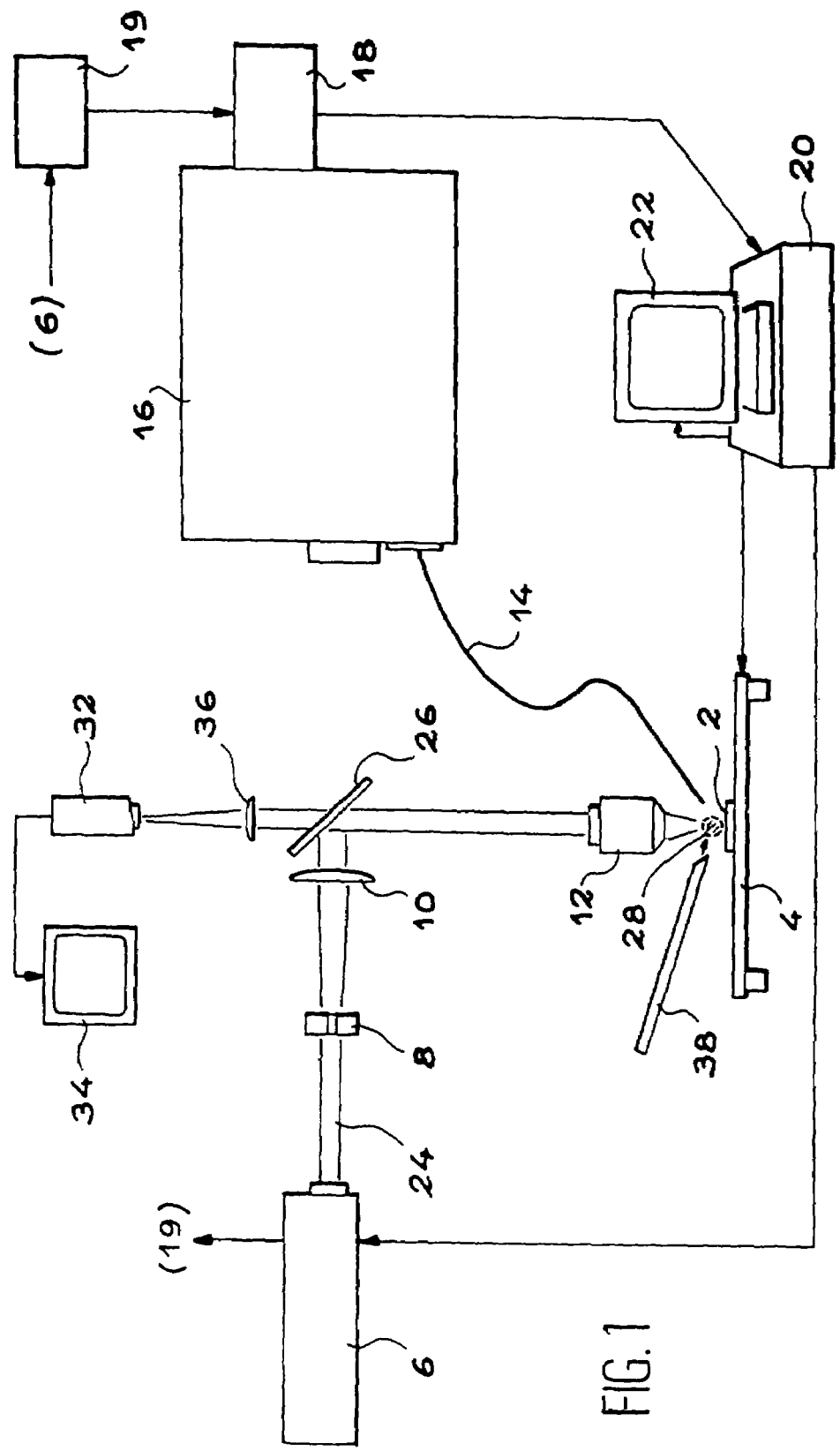
FIG. 1 is a diagrammatic view of a particular embodiment of the device for optical emission spectrometry on laser produced plasma according to the invention, and FIG. 2 diagrammatically illustrates an installation for analysis of MOX fuel pellets using the device in FIG. 1.

FIG. 1 shows a diagrammatic view through an example device for optical emission spectrometry on laser produced plasma according to the invention and adapted to the microanalysis of MOX pellets.

As we have already seen, the nature of the test pieces to be analysed is different. One of the test pieces (the unbaked compound) is brittle, while the second (the sintered compound) is a dense material and is difficult to ablate. The device in FIG. 1 is designed specifically for satisfactorily ablating sintered test pieces and unbaked pellets.

This device is intended for the analysis of MOX pellets such as pellet 2 and comprises a plate 4 on which the pellet is placed. It is a plate capable of micro-displacements along two perpendicular directions X and Y.

The device also comprises a pulsed laser 6, a diaphragm 8, a convergent lens 10, a focusing objective 12, an optical fibre 14, a spectrometer 16 equipped with a detection system 18 and a computer 20 equipped with a display screen 22.

All these components will be described in more detail later.

The choice of the wavelength of the laser used 6 is imposed by the nature of the materials to be analysed. It is a laser that emits in the ultraviolet to obtain the best laser-material coupling for ablation of materials.

In the example considered, the laser 6 is a solid Nd-YAG laser with frequency quadrupling, capable of emitting laser pulses with a duration of a few nanoseconds. Its wavelength is equal to 266 nm. At this wavelength, it is capable of "depositing" powers per unit area greater than 10 GW/cm$^2$.

The choice of operation in "mono firing" (in other words using a single laser pulse to create each impact) necessitates a very stable energy in each pulse (relative energy variation not exceeding 5%).

This need means that a compact low energy laser (about 2 mJ at 266 nm) should be chosen providing sufficiently stable energy.

The energy deposited on the target is less than a few hundred microjoules due to the spatial filtering.

This energy, focused on areas of a few µm$^2$, makes it possible to achieve sufficient irradiance (power per unit area) for ablation of the sintered MOX pellet.

Furthermore, the compactness of the laser facilitates its integration into an industrial environment.

Its ability to operate in a stable and reproducible manner at a frequency equal to or greater than 15 Hz makes it possible to acquire maps at the rate necessary for inspection of the MOX pellet manufacturing process.

The beam 24 emitted by laser 6 is spatially filtered by the diaphragm 8; the aperture of this diaphragm may be smaller than the aperture of beam 24, and capable of selecting the central part of this beam 24. If necessary, the beam diameter may be adapted using a telescope type optical set-up.

Note that this beam is not focused in the plane of the diaphragm.

For example, the convergent lens 10 consists of a convergent compound lens that projects the image of diaphragm 8 to infinity.

The laser beam thus obtained is then directed by a dielectric mirror 26 onto the focusing objective 12 designed to focus this laser beam onto the pellet 2.

It is a refractive microscope objective assembled without glue, antireflection treated for reflections at the emission wavelength of the laser 6 (266 nm in the example considered) and capable of resisting the light flux output from laser 6 without damage.

Note that the image of diaphragm 8 projected to infinity by lens 10 is applied to the objective 12, and this objective focuses this image onto the pellet 2.

Furthermore, the assembly formed by the diaphragm, the lens 10 and the objective 12 satisfies the following conditions:

the image of the diaphragm focused on the pellet is equal to the required dimension on this pellet and the focal point of the laser beam passes through the diaphragm, the lens 10 and the objective 12, and is then outside the image plane of the diaphragm.

This objective 12 also has a large numerical aperture, greater than or equal to 0.1. This choice prevents interaction of the laser beam with the plasma 28 generated during laser ablation.

This interaction phenomenon causes fluctuations in plasma production and reduces the reproducibility performances, which is not good for the production of quantitative maps.

Furthermore, this objective 12 has an optical resolution of 1 µm such that the image of the diaphragm can be focused on the surface of the pellets without any significant optical aberration. These characteristics are important to achieve focusing of the laser beam on a diameter of 3 µm. This spatial resolution of the analytic probe is necessary to be able to quantitatively describe objects with a size of 10 µm.

This type of lens associated with the ablation wavelength of 266 nm and with a minimum irradiance of 10 $GW/cm^2$, is a technical solution that enables controlled and localized ablation of sintered materials.

The objective 12 is supported by a microscope frame, not shown. This focusing objective 12, associated with the diaphragm 8 that is placed at the focal point of the lens 10—objective 12 assembly, is capable of achieving ablation craters with a diameter of 1 µm or less.

The position of the pellet 2 at the focal point of the laser beam is checked by viewing the area of this pellet 2 through the mirror 26 using a CCD camera 32 associated with a display screen 34 and located above the dielectric mirror 26 that is treated at the laser wavelength.

The focusing plane of the CCD camera coincides with the focusing plane of the laser beam.

The lens 36 located between the mirror 26 and the camera 32 is used to produce the image of the surface of the test piece on the camera 32.

This camera 32 is used to select the area to be analysed and to place the surface of the test piece on the plane of the image of the diaphragm 8 formed by the objective 12.

The pellet to be analysed 2 is placed with an accuracy of one micrometer on the microdisplacement plate fitted with motor drive along the two perpendicular axes X and Y.

Displacement in the XY plane is a means of choosing the area to be mapped and mapping the pellet.

After each laser pulse, the plate is moved automatically by a predefined distance (measurement pitch). The laser impacts may be adjacent (displacement equal to the diameter of the ablation crater) or not adjacent, depending on the chosen pitch.

The plate displacement may be controlled using a positioning control handle (not shown) or directly by control software contained in the computer 20.

The displacement frequency of the plate between two measurement points is greater than or equal to 15 Hertz. This displacement frequency is one of the important characteristics of the device in FIG. 1, since it can be used to make inspections of the MOX pellet fabrication process with a sufficiently large number of test pieces.

The optical emission of the plasma 28 is collected by the optical fibre 14, one end of which is held in place by means not shown and is placed close to the formation area of the plasma 28 produced by interaction of the laser beam with the pellet 2. The other end of the optical fibre is connected to the input of the optical spectrometer 16.

The resolution of this spectrometer 16 is high: the full width at half maximum of the peaks that it produces is greater than 0.05 nm. This type of resolution is necessary for the analysis of plutonium and uranium emission spectra, since these spectra contain a large number of lines.

Collection of light using an optical fibre makes it possible to work remotely and avoids the need for the user of the device to be close to the area in which radioactive test pieces are handled at all times. This collection mode contributes to the safety of the technique for analysis of MOX pellets according to the invention.

The spectrometer 16 is coupled to the detection system 18 that is composed of a CCD camera equipped with an intensifier. The spectral range accessible with this detection system 18 varies from 190 nm to 800 nm. The spectral measurement window is equal to about 10 nanometers.

A pulse generator 19 opens the camera intensification door of the system 18 after a timeout that is chosen as a function of the laser pulses.

The laser 6, the micro-displacement plate 4, the spectrometer 16 and the detection system 18 are controlled using the computer 20 that is equipped with an appropriate control software.

The required performances cannot be achieved without an appropriate measurement sequence. The detection system 18 makes a measurement only during a measurement time interval determined after each pulse emitted by the laser (for time resolution reasons). The choice of this measurement interval is very important for the application considered in this case (analysis of MOX fuel pellets).

A very bright plasma (spark) is created at the beginning of the laser-material interaction, and the optical signal from this plasma cannot be used. The measured optical emission from the elements becomes unusable after the end of this black body radiation emission, with a continuous wavelength.

Maps of MOX pellets are made using a spatial resolution of 3 µm and are obtained at a measurement interval or "gate" from 100 ns to 1 µs, this "gate" being opened for 10 ns to 500 ns after emission of a laser pulse.

After the emission due to the impact of this laser pulse on the pellet 2 has been detected, the computer 20 sends a displacement order to the plate 4. Once this displacement has been made, a new measurement sequence is started.

The software installed on the computer 20 can be used to select the median wavelength of the spectrum to be recorded and to choose the dimension of the area to be analysed, and the measurement pitch.

This software records the spectrum over a spectral range of about 10 nm each time that the laser is fired.

The optical emission lines that are characteristic of uranium and plutonium can then be used.

Means comprising a duct 38 are provided to project a jet of a gas such as argon towards the surface of the analysed pellet 2 to increase the plasma optical emission signal.

Document [1] mentioned above contains more information about this subject.

As a result, the intensity of the optical emission lines can be multiplied by a coefficient of 10 or more (2.5 to 3 for a microplasma see document [1]) compared with optical spectrometry in a natural atmosphere without an argon jet.

Note that a calibration is made to determine the relation between the intensity of the emission signal and the concentration of the chemical elements in the analysed pellets. This sampling is checked daily to make sure that the measurements made are accurate.

This calibration is made using reference test pieces of sintered MOX pellets. These test pieces are produced by mixing oxide powders according to a fabrication process that can give sufficiently uniform reference test pieces.

The calibration is made by making about a hundred measurements using successive laser pulses, distributed at random on the surface of reference test pieces.

The dispersion of the measurements is of the order of the dispersion of the technique used, in other words about 4% to 5%.

The spectrum usage software determines the value of gross and net intensities of the emission lines selected in the spectral measurement range.

The calibration curves are drawn up with the values of the intensities of emission lines of each chemical element or intensity ratios of emission lines of the two elements (Pu and U) contained in the pellets.

For each laser impact, the intensity values of the lines (or the line ratios) are transformed into absolute concentrations making use of calibration curves.

The concentration distribution of each chemical element at the pellet surface is converted into a coloured image by an image processing software.

Each concentration range is represented by a colour.

The elementary maps of mixed oxide pellets $PuO_2/UO_2$ are produced using a device according to the invention, this device being adapted to the manipulation of radio elements.

The focusing objective 12 and the microdisplacement plate 4 are then placed in a confinement containment, for example a glove box.

Figure 2:
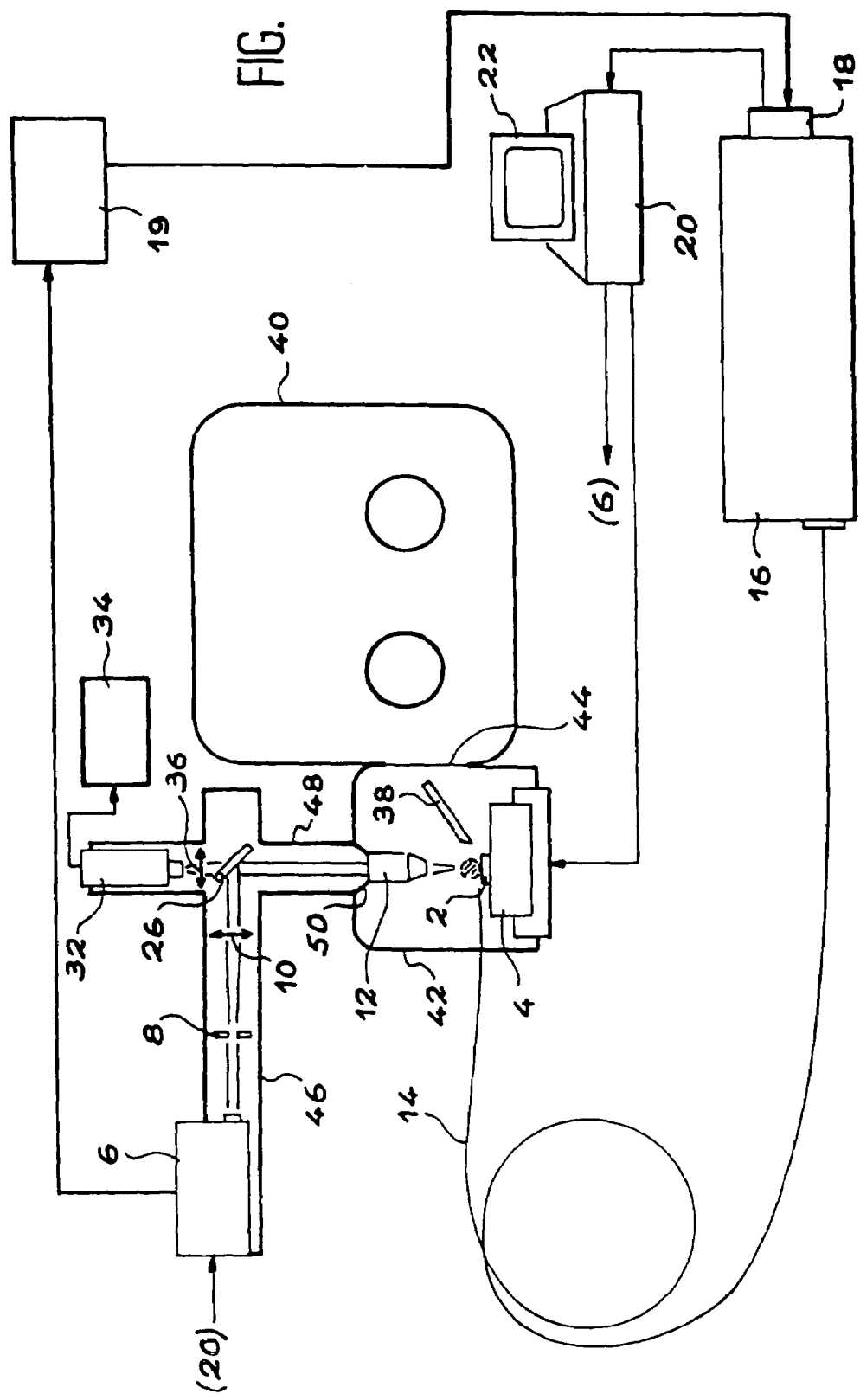

FIG. 2 shows a diagrammatic view of such a device that can be used to make elementary maps of mixed $PuO_2/UO_2$ pellets.

This figure shows the components described above with reference to FIG. 1. Furthermore, the device shown in FIG. 2 comprises:
   a first confinement containment 40 into which the pellets that are to be analysed are entered, and
   a second confinement containment 42 connected to the first containment 40 through an airlock 44 that is used to transfer a pellet to be analysed from containment 40 to containment 42.

The second containment 42 contains the focusing objective 12 and the microdisplacement plate 4.

Each pellet is put back into containment 40 after having been measured with the device.

FIG. 2 also shows the ducts 46 and 48 connecting the laser 6 and the camera 32 to the second containment 42.

The duct 46 contains the diaphragm 8 and the lens 10, and the duct 48 contains the mirror 26 and the lens 36.

A sealed confinement wall 50 presses around the periphery of the objective 12 isolating the inside of the containment 42 of these ducts 46 and 48, while allowing the laser beam to pass as shown in FIG. 2.

The invention is not limited to the inspection of MOX fuel pellets. It is applicable to the elementary analysis of any test piece or object for which it is required to know the component elements with impact size resolutions of up to 1 µm.

For information, and in no way restrictively:
   the aperture of the diaphragm is circular and its diameter is 250 µm,
   the focal length of the lens 10 is 1000 mm,
   the digital aperture of the microscope objective 12 is close to 250, and its magnification is determined as a function of the required diameter for the impact points.

The invention claimed is:

1. Elementary analysis device by optical emission spectrometry on laser produced plasma, the device comprising:
   a pulsed laser source;
   a diaphragm having an aperture of a fixed diameter for selecting part of a laser beam emitted by said pulsed laser source on an object to be analysed, said laser beam not being focused in the plane of said diaphragm,
   first optical means projecting the image of the diaphragm to infinity,
   second optical means receiving the image of said diaphragm projected to infinity by said first optical means and focusing it on said object to be analysed to produce plasma on the surface of, said object,
      wherein the image of said diaphragm focused on said object is equal to a required dimension on said object, said required dimension corresponding to a required spatial resolution; and
      the focal point of said laser beam, after crossing through said diaphragm and said first and second optical means, is outside the image plane of the diaphragm;
   means for analyzing a light radiation spectrum emitted by the plasma, said means for analyzing disposed adjacent to the plasma;
   means for determining the elementary composition of said object from the means for analyzing a light radiation spectrum; and
   means for displacing said object within a plane after each pulse of said laser source.

2. Device according to claim 1, wherein said second optical means have a numerical aperture equal to approximately 0.1 or greater.

3. Device according to claim 1, wherein an impact size of the laser beam on the object is greater than or equal to 1 µm.

4. Device according to claim 1, further comprising means for displacing the object between two laser pulses at a displacement frequency of the object between two laser pulses of the source is greater than or equal to 15 Hz.

5. Device according to claim 1, wherein the pulsed laser source emits ultraviolet light.

6. Device according to claim 1, wherein a relative variation of energy between one laser pulse and the next does not exceed 5%.

7. Device according to claim 1, wherein said diaphragm comprises a circular aperture for selecting the central part of the laser beam output from the laser source, said first optical means comprise refractive optical means, and said second optical means comprise refractive optical means having a microscope objective.

8. Device according to claim 7, wherein said first and second optical means are antireflection treated at the wavelength of the light emitted by said pulsed laser source.

9. Device according to claim 1, further comprising means for blowing a gas jet onto the object.

10. Device according to claim 1, further comprising:
   means for observing said object, so that said object can be placed in the image plane of said diaphragm, and a mirror reflecting at the wavelength of said pulsed laser source and transparent at other wavelengths, said mirror being placed on the light path between said first and second optical means and designed to reflect almost the entire laser beam to said second optical means and to transmit an image of said object to said means for observation.

11. Device according to claim 2, wherein the impact size of the laser beam on said object is greater than or equal to 1 μm.

12. Device according to claim 3, wherein said object has a displacement frequency between two laser pulses of said laser source, said displacement frequency being greater than or equal to about 15 Hz.

13. Device according to claim 6, wherein said diaphragm (8) comprises a circular aperture for selecting the central part of the laser beam output from the laser source, said first optical means are refractive optical means, and said second optical means are refractive optical means comprising a microscope objective (12).

14. Device according to claim 8, further comprising means (38) for blowing a gas jet onto said object (2).

15. Device according to claim 1, wherein said diaphragm is also usable for delimiting the shape of the impact of the laser beam on an object to be analyzed.

* * * * *